United States Patent [19]
Asogawa et al.

[11] Patent Number: 5,290,568
[45] Date of Patent: Mar. 1, 1994

[54] PRODUCTION OF β-FORM THIAMINE HYDROCHLORIDE CRYSTALS

[75] Inventors: Tatsuo Asogawa, Kishiwada; Yoshitomi Kakiguchi, Kawanishi; Seiji Izuhara, Tondabayashi, all of Japan

[73] Assignee: Takeda Chemical Industries, Ltd., Osaka, Japan

[21] Appl. No.: 945,728

[22] Filed: Sep. 15, 1992

[30] Foreign Application Priority Data

Sep. 19, 1991 [JP] Japan .................. 3-239765

[51] Int. Cl.$^5$ .................. A61K 9/14; A61K 31/51
[52] U.S. Cl. .................. 424/489; 514/951; 514/952
[58] Field of Search .................. 424/489, 464, 465; 514/276

[56] References Cited

U.S. PATENT DOCUMENTS 4,702,919 10/1987 Kitamori et al. .................. 424/480

*Primary Examiner*—Thurman K. Page
*Assistant Examiner*—James M. Spear
*Attorney, Agent, or Firm*—Wenderoth, Lind & Ponack

[57] ABSTRACT

A method of producing β-form thiamine hydrochloride crystals which comprises moistening α-form thiamine hydrochloride crystals in the presence of β-form thiamine hydrochloride crystals as seed crystals and stirring the mixture and a method of producing pharmaceutical preparations containing β-form thiamine hydrochloride crystals which comprises moistening α-form thiamine hydrochloride crystals, together with a binder, with water in the presence of β-form thiamine hydrochloride crystals as seed crystals and stirring the mixture.

β-Form thiamine hydrochloride crystals which are stable and resistant to caking and pharmaceutical preparations containing the same can be produced in a simple and easy manner.

6 Claims, 2 Drawing Sheets

PRODUCTION OF β-FORM THIAMINE HYDROCHLORIDE CRYSTALS

FIELD OF THE INVENTION

This invention relates to a method of producing β-form crystals of thiamine hydrochloride (hereinafter referred to as β form for short) from α-form crystals of thiamine hydrochloride (hereinafter referred to as α form briefly).

BACKGROUND OF THE INVENTION

In many instances, thiamine hydrochloride is administered in solid dosage forms, typically of tablets, either singly or in combination with one or more other vitamins and/or some other drug or drugs.

These solid dosage forms are required to maintain their quality until administration. Therefore, thiamine hydrochloride should desirably be stabilized against heat and moisture. Commercially available grades of thiamine hydrochloride, which are mostly in the α form, are not always stable against heat or moisture absorption as desired. Therefore, in the prior art, measures have been taken to protect them from heat and moisture as much as possible for securing their quality.

OBJECT OF THE INVENTION

For insuring the acceptable quality of thiamine hydrochloride and other drugs, various contrivances have heretofore been made from dosage form and packaging viewpoints. It is evident, however, that a radical solution is to render thiamine hydrochloride itself more stable. It would be a neat solution if a commercial α-form thiamine hydrochloride itself could be transformed into the β form which is nonhygroscopic, with little tendency toward caking, namely good caking resistance, and has higher heat stability.

A readily conceivable method for converting the α form to the β form would comprise dissolving the α form in a solvent and adding, prior to recrystallization, β-form crystals as seeds to the solution. However, this method requires the solvent in large amounts and is time-consuming and uneconomical. When an organic solvent is used, the residual solvent in the product presents a problem of its own. Therefore, such method is not an advantageous method for industrial application.

Accordingly, it is an object of the present invention to provide a simple and easy and industrially practicable method of converting the α form to the β form.

SUMMARY OF THE INVENTION

Figure 1:
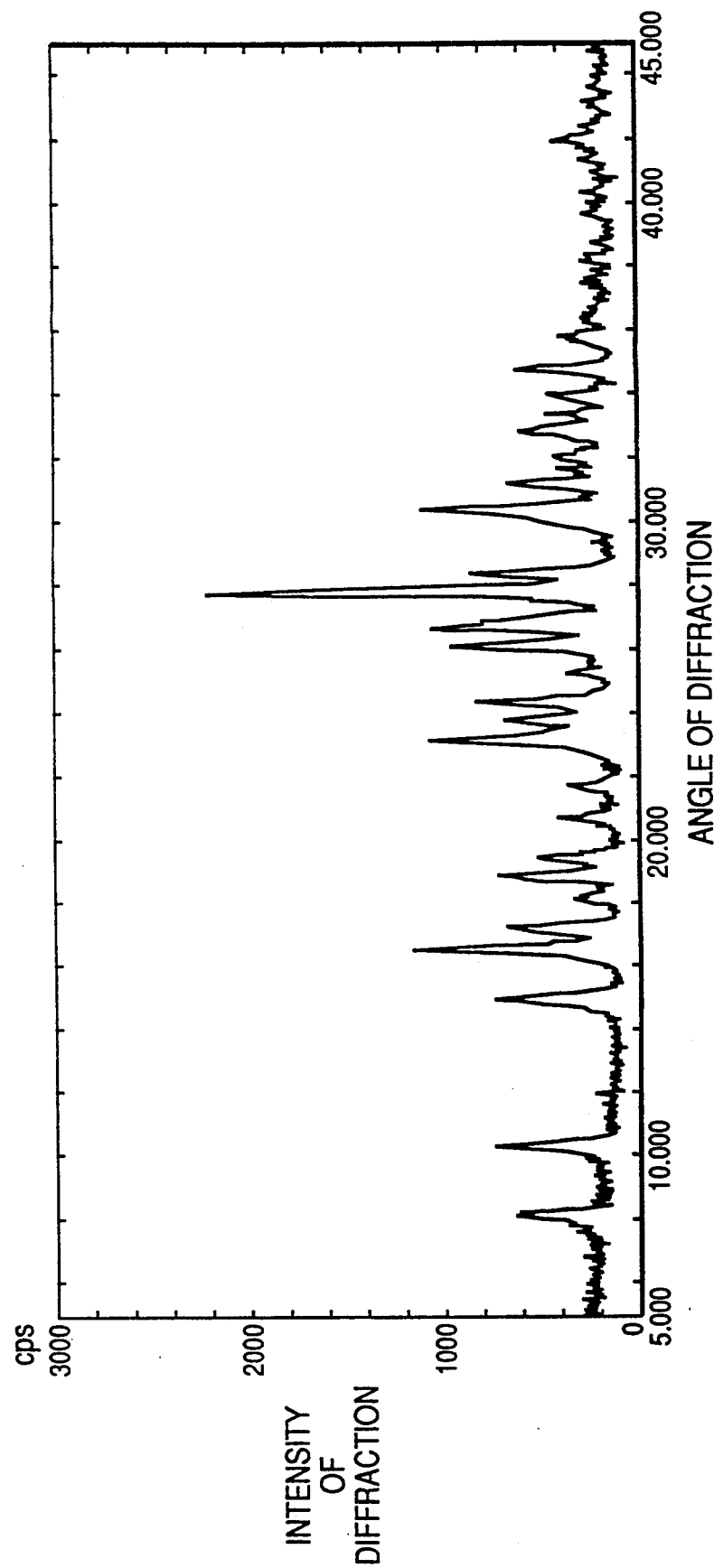
[FIG. 1] A powder X ray diffraction pattern (CuKα, 40 kV, 40 mA) for the β-form crystalline thiamine hydrochloride granules obtained in Example 1.

The present inventors made intensive investigations to solve the above problems and, as a result, unexpectedly found that addition of a small amount of water and powdery β-form crystals to the α form followed by mere stirring causes conversion of the whole amount of the α form to the β form in a short period of time. Further investigations based on this finding have now led to completion of the present invention.

The invention thus provides:

(1) a method of producing β-form thiamine hydrochloride crystals which comprises moistening α-form thiamine hydrochloride crystals with water in the presence of β-form thiamine hydrochloride crystals as seed crystals and stirring the resulting moistened mixture;

(2) a method as described above under (1), wherein a crystalline powder of α-form thiamine hydrochloride not less than about 95 weight percent of which passes through a 100-mesh sieve is used as the α-form thiamine hydrochloride;

(3) a method as described above under (1), wherein a crystalline powder of α-form thiamine hydrochloride not less than about 95 weight percent of which passes through a 145-mesh sieve is used as the α-form thiamine hydrochloride;

(4) a method as described above under (1), wherein the α-form thiamine hydrochloride is moistened with about 1 to 15 weight percent, relative to the weight of said α-form thiamine hydrochloride, of water;

(5) a method as described above under (1), wherein the β-form thiamine hydrochloride is added in an amount of about 1 to 30 weight percent based on the weight of the α-form thiamine hydrochloride;

(6) a method of producing pharmaceutical preparations containing β-form thiamine hydrochloride crystals which comprises moistening α-form thiamine hydrochloride crystals and a binder with water in the presence of β-form thiamine hydrochloride crystals and stirring the resulting moistened mixture;

(7) a method as described above under (6), wherein the binder is used in an amount of about 0.5 to 5 weight percent based on the weight of the thiamine hydrochloride used.

(8) granules which contain β-form thiamine hydrochloride crystals in an amount of not less than 90 weight percent relative to the weight of the total granules on the dried basis and (9) tablets obtained by compressing a tableting mixture comprising granules which contain β-form thiamine hydrochloride crystals in an amount of not less than 90 weight percent relative to the weight of the total granules on the dried basis.

DETAILED DESCRIPTION OF THE INVENTION

The starting material α-form thiamine hydrochloride may be powdery or granular and may vary in granular size provided that it is crystalline. In particular, an α-form thiamine hydrochloride powder at least about 95 weight percent of which passes through a 100-mesh (JIS) sieve is desirable and more preferably, an α-form thiamine hydrochloride powder at least about 95 weight percent of which passes through a 145-mesh (JIS) sieve is desired. Water is suitably added in an amount such that it is present in an amount of about 1 to 15 weight percent, preferably about 1.4 to 8 weight percent, relative to α-form thiamine hydrochloride. Said β-form thiamine hydrochloride is preferably added as a kind of seed crystal and the level of addition thereof may vary dependent on the amount of water added (there is a general tendency that the addition level may be reduced when water is used in larger amounts). From the economical efficiency viewpoint, however, addition of the β form seeds in an amount of 1 to 30 weight percent, preferably 5 to 20 weight percent, will be sufficient to promote uniform conversion to the β form.

In producing β-form thiamine hydrochloride, namely β form, in accordance with the invention, one or more of such additives as binders, stabilizers, colorants, corrigents and diluents may be added, if necessary, in preparation for the manufacture of β form-containing dosage forms.

The conversion of the α form to the β form is generally promoted by applying some or other mechanical stimulus, for example stirring or agitation, mixing or blending, or vibration, to the above components. Generally, stirring or mixing is preferred. The stirring or mixing is conducted in the conventional manner. While stirring in a mixer or the like in common use for about 10 minutes or longer generally allows substantially complete conversion of the α form to the β form, the intensity of stirring or mixing may be influential, hence the mixing time should preferably be adjusted so as to attain complete conversion to the β from. After mixing, the conversion product may be dried in the conventional manner, for example by fluidized bed drying, ordinary drying or vacuum drying, and granulated to give a final product.

As the conventional stirring or mixing technique, there may be mentioned, for example, the fluidized bed technique, centrifugal flow technique, tumbling technique, grinding technique, kneader technique and stirring technique, each using a mixer suited for its application.

The addition of water may be effected by spraying or by adding at one time. The above-mentioned steps of mixing, water addition, drying and granulation may be combined in a suitable manner and the order of such steps may be changed.

As a preferred combination, there may be mentioned a process comprising mixing with spraying, granulating and drying using a fluidized bed granulator, for instance.

In the present method, moistening and mixing for conversion of α form to β form can be, in general, carried out at room temperature to about 80° C., usually at room temperature. However, in a combined process comprising mixing with spraying, granulating and drying using a fluidized bed granulator as a typical process as mentioned above, the process is carried out usually at about 40° C. to about 80° C., preferably at about 50° C. to 70° C.

A water-soluble binder or an organic solvent-soluble binder may be used as the binder for granulation.

The water soluble binder includes, among others, pregelatinized starch, water-soluble cellulose derivatives and water-soluble macromolecules. The term "pregelatinized starch" includes products obtained by dispersing starch in water and heating the dispersion, and dried products derived therefrom. The pregelatinized starch includes, among others, pregelatinized corn starch, pregelatinized potato starch, pregelatinized modified starch [e.g. those described in the Code of Federal Regulation (U.S.A.) § 12.1.1031 a, b, c, d, e, f, g or h, etc.], and gelatinized and dried commercial starch products such as Amikol C (Nichiden Kagaku K.K.), Pre-Gel (Hublinger Co., U.S.A.) and Instant Clearjel National Starch & Chemical Corp., U.S.A.).

The water-soluble cellulose derivatives include hydroxypropylcellulose, hydroxymethylcellulose, hydroxypropylmethylcellulose, carboxymethylcellulose, methylcellulose, etc., and the water-soluble macromolecules include polyvinylpyrrolidone, polyvinyl alcohol, dextrin, gum arabic, gelatin, etc.

As the organic solvent-soluble binder, there may be mentioned, for example, organic solvent-soluble cellulose derivatives (e.g. cellulose acetate phthalate, hydroxypropylmethylcellulose phthalate, ethylcellulose, etc.).

As the solvent for dissolving the above-mentioned binder to be added in the practice of the invention, there may be mentioned water and organic solvents [e.g. alcohols (e.g. methyl alcohol, ethyl alcohol, isopropyl alcohol), acetone, etc.] that can dissolve the binder.

The concentration of the binder to be added may be set in a practical range, for example, in a range of about 1 to about 10 weight percent. It may vary depending on the combination of binder and solvent and should preferably be such that a viscosity suited for binder addition, for example about 1 to 1,000 cps, can be obtained. The binder addition may be carried out in any step. Thus, the binder may be admixed in advance with the α form or added to the product β form in the step of granulation.

After granulation, the product is dried by a conventional method. Thus, it may be dried, after completion of spraying, by feeding fluidizing air alone and thereby maintaining the fluidized state until the product temperature arrives at a certain predetermined level.

The dried product as such occurs as granules. If desired, the agglomerate may be crushed in a crusher such as a power mill or Fitz mill to give granules with a desirable grain size distribution.

The method of the present invention is advantageously applied, in particular, to the manufacture of direct compression preparations (granules, tablets etc.) having a high thiamine hydrochloride content. Particularly, there can be produced granules which contain β-form thiamine hydrochloride crystals in an amount of not less than 90%, preferably about 97%. For instance, when α-form thiamine hydrochloride crystals, together with a binder, are moistened with water and stirred, β form-containing granules for direct compression tableting can be readily obtained. Further, tablets can be produced by a conventional method. For example, tablets can be obtained by compressing a tableting mixture comprising such granules as mentioned above, i.e. granules which contain β-form thiamine hydrochloride crystals in an amount of not less than 90%. As a more specific example of the method of producing such preparations, there may be mentioned the method comprising spraying α form with an aqueous binder solution while fluidizing said form in a fluidized bed granulator in the presence of β form as seed crystals to thereby moisten the whole mixture with water, followed by drying, to give granules. Further, thus-obtained granules are mixed with conventional excipients such as lactose, magnesium stearate, corn starch and talc, and the mixture is tableted by a tablet machine to obtain tablets.

A simple and easy method of producing β-form thiamine hydrochloride crystals which are superior to α-form thiamine hydrochloride crystals in stability, hygroscopicity and caking resistance (i.e. little tendency toward caking) is provided.

The following examples are further illustrative of the present invention.

Example 1

Figure 2:
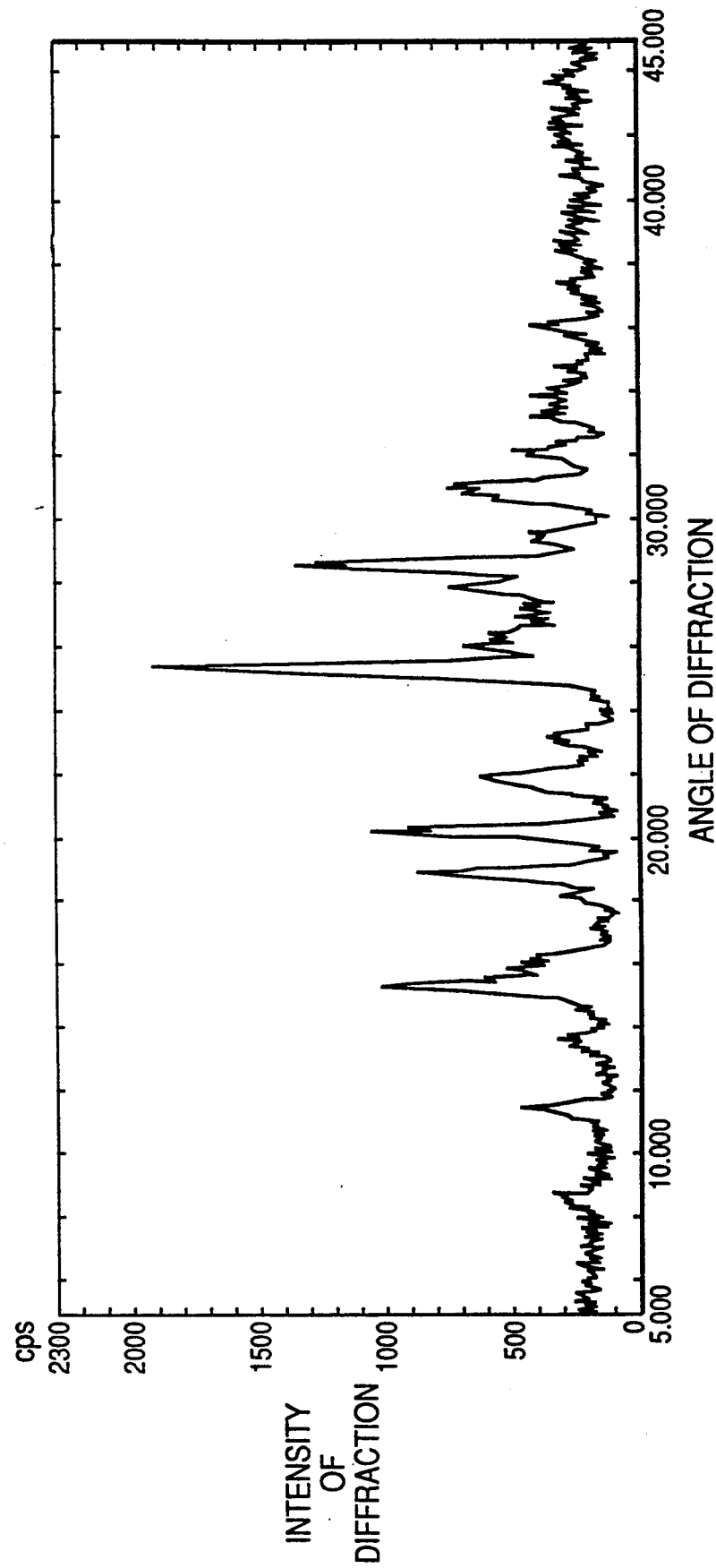
[FIG. 2] A powder X ray diffraction pattern (CuKα, 40 kV, 40 mA) for the α-form thiamine hydrochloride crystals used as the starting material in Example 1.

A model FD-3S fluidized bed granulator (Powrec) was charged with 2 kg of an α-form powder 96% of which passed through a 145-mesh (JIS) sieve and 200 g of a β-form powder. While being fluidized at an air supply rate of 0.5 m /min. at 60° C., the mixture was sprayed with 1.2 liters of a 7% aqueous solution of hydroxypropylmethylcellulose and then dried to obtain granules (a mixture of granules and powders, hereinafter referred to as granules). Crystals form analysis based on a DSC chart (obtained by using a SEIKO Instrument model SSC/5200 instrument) revealed that the dried granules thus obtained was composed exclusively of β-form crystals. A powder X ray diffraction pattern (CuKα, 40 kV, 40 mA) for the dried β form powder obtained is shown in FIG. 1. A powder X ray diffraction pattern (CuKα, 40 kV, 40 mA) for the starting material α form powder is shown in FIG. 2.

Example 2

A kneader was charged with 2 kg of an α-form powder 98% of which passed through a 145-mesh (JIS) sieve and 150 g of the β form, followed by addition of 200 g of water. The charge was kneaded for 60 minutes to give a kneaded mixture. Crystal form analysis based on a DSC chart for the kneaded mixture revealed that said powder was wholly composed of β-form crystals.

Example 3

A kneader was charged with 1 kg of an α-form powder not less than 95% of which passed through a 145-mesh (JIS) sieve and 50 g of a β-form powder, followed by addition of 70 g of a 5% aqueous solution of dextrin. The charge was blended for 30 minutes to give granules. Crystal form analysis of the mixed granules based on a DSC chart therefor revealed that the granules consisted exclusively of β-crystals.

Comparative Example 1

The procedure of Example 1 was followed but the addition of the β form as seed crystals was omitted. The mixed granules obtained contain scarcely any β form but were composed substantially of α-form crystals

Comparative Example 2

The procedure of Example 2 was followed but the addition of the β form was omitted. The kneaded mixture obtained was composed substantially of α-form crystals.

Comparative Example 3

The procedure of Example 3 was followed but the addition of the β form was omitted. The granules obtained were composed substantially of α-form crystals.

Comparative Example 4

The procedure of Example 3 was followed by the addition of water was omitted. The granules obtained were composed substantially of α-form crystals.

Example 4

Using β form granules obtained in Example 1 (β-form thiamine hydrochloride 97%, hydroxymethylcellulose 3%), tablets were produced in accordance with the following formulation and tableting conditions.

| Formulation: | |
| --- | --- |
| β form granules | 53.1 mg |
| Lactose | 145.9 mg |
| Magnesium stearate | 1.0 mg |
| | 200.0 mg |

Tableting Conditions:
Tablet machine: KIKUSUI CLEANPRESS Correct 6HUK
Die, Punch: 8.5 mm in diameter, Curveture radius 12 mm
Rotation speed: 40 rpm
Main Compression Force: 1000 kg
Pre-Compression Force: 300 kg

Comparative Example 5

Using α form granules obtained in Comparative Example 1 (α-form thiamine hydrochloride 97%, hydroxypropylcellulose 3%) in place of β form granules, tablets were produced in accordance with the same formulation and tableting conditions as in Example 4.

Test Example

For comparison of the tablets of β form as obtained in Example 4 in accordance with the present invention with the tablets of α form as obtained in Comparative Example 5 in stabilities, after the respective tablets were preserved on the following conditions for the following period, the residual percentages of thiamine hydrochloride in the respective tablets were estimated by means of high performance liquid chromatography (HPLC). The results are shown in the following table.

TABLE

| Preservation Conditions | Preservation Period | Residual Percentage | |
| --- | --- | --- | --- |
| | | Example 4 | Comparative Example 5 |
| Dry-heated (40° C.) | 8 weeks | 98.9 | 93.6 |
| Humid-heated (40° C., Relative humidity: 75%) | 8 weeks | 95.0 | 82.9 |

We claim:

1. A method of producing β-form thiamine hydrochloride crystals which comprises moistening α-form thiamine hydrochloride crystals with water in the presence of about 1 to 30 weight percent, based on the weight of the α-form thiamine hydrochloride, β-form thiamine hydrochloride crystals as seed crystals and agitating the resulting moistened mixture.

2. A method as claimed in claim 1, wherein a crystalline powder of α-form thiamine hydrochloride not less than about 95 weight percent of which passes through a 100-mesh sieve is used as the α-form thiamine hydrochloride crystals.

3. A method as claimed in claim 1, wherein a crystalline powder of α-form thiamine hydrochloride not less than about 95 weight percent of which passes through a 145-mesh sieve is used as the α-form thiamine hydrochloride crystals.

4. A method as claimed in claim 1, wherein the α-form thiamine hydrochloride crystals are moistened with about 1 to 15 weight percent, relative to the weight of said α-form thiamine hydrochloride crystals, of water.

5. A method of producing a pharmaceutical preparation containing β-form thiamine hydrochloride crystals which comprises moistening α-form thiamine hydrochloride crystals and a binder with water in the presence of about 1 to 30 hydrochloride, β-form thiamine hydrochloride crystals as seed crystals and stirring the resulting moistened mixture.

6. A method as claimed in claim 5, wherein the binder is used in an amount of about 0.5 to 5 weight percent based on the weight of the α-form thiamine hydrochloride used.

* * * * *